(12) United States Patent
Köpke

(10) Patent No.: US 7,197,350 B2
(45) Date of Patent: Mar. 27, 2007

(54) DEVICE FOR DETERMINING ACOUSTICALLY EVOKED BRAINSTEM POTENTIALS

(75) Inventor: Wolfgang Köpke, Berlin (DE)

(73) Assignee: Maico Diagnostic GmbH, Berlin (DE)

( * ) Notice: Subject to any disclaimer, the term of this patent is extended or adjusted under 35 U.S.C. 154(b) by 82 days.

(21) Appl. No.: 10/471,057

(22) PCT Filed: Mar. 7, 2002

(86) PCT No.: PCT/EP02/02533

§ 371 (c)(1),
(2), (4) Date: Jan. 15, 2004

(87) PCT Pub. No.: WO02/071937

PCT Pub. Date: Sep. 19, 2002

(65) Prior Publication Data

US 2004/0122303 A1    Jun. 24, 2004

(51) Int. Cl.
*A61B 5/0478* (2006.01)

(52) U.S. Cl. .................................................... 600/383

(58) Field of Classification Search ................. 600/383, 600/559; 607/136, 139
See application file for complete search history.

(56) References Cited

U.S. PATENT DOCUMENTS

| 3,659,614 A * | 5/1972 | Jankelson .................. 607/139 |
| 5,740,812 A | 4/1998 | Cowan |
| 5,954,667 A | 9/1999 | Finkenzeller et al. |
| 6,154,669 A | 11/2000 | Hunter et al. |

\* cited by examiner

*Primary Examiner*—Lee S. Cohen
(74) *Attorney, Agent, or Firm*—Dykema Gossett PLLC

(57) ABSTRACT

The invention relates to a device for determining acoustically evoked brain potentials in objective audiometry from electrodes applied to the head of a subject, where the device comprises a plurality of electrodes, i.e. at least one pickup electrode and a reference electrode, to be applied at different points of the head, where the electrodes are mounted on a structure in fixed positions in relation to each other, where the structure comprises at least one flexible cushion abutting the head of the subject around an ear, where the pickup electrode and the reference electrode are integrated in the flexible cushion.

7 Claims, 5 Drawing Sheets

DEVICE FOR DETERMINING ACOUSTICALLY EVOKED BRAINSTEM POTENTIALS

BACKGROUND OF THE INVENTION

The derivation of acoustically evoked electrical brain potentials of a subject is a known audiometric diagnostic method for testing healing and for evaluating various causes of hearing damage without the active participation of the subject.

This method is referred to in the field as ERA (electric response audiometry) or BERA (brainstem electric response audiometry) or brainstem audiometry. Areas of application for this method include for example the performance of the first hearing tests in newborns, testing the hearing of infants or of unconscious persons such as accident victims for example, and the diagnosis of neurologic diseases, for example nearinomas of the acoustic nerve. Intraoperative hearing tests are also possible with this method.

Electrical brain potentials are triggered by acoustic stimulation of the ear with conduction through air or bone. Headphones are usually used for the purpose. The electrical signals that are thus generated by the brainstem are picked up by electrodes applied to the head. Usually three electrodes are used, namely one electrode to determine the reference potential and two active electrodes to derive the acoustically-evoked electrical signals at two different locations on the head.

Acoustic stimulation of the ear can take, for example, the form of click stimuli or, for direct determination of the hearing threshold, of a rapid sequence of clicks with increasing volume. Other types of stimuli are of course also possible. The brainstem generates potential waves at each click which are averaged after being picked up and conducted away by the electrodes.

Previously, the electrodes were usually glued or attached mechanically in some other fashion individually to the head. Firstly, this is time-consuming and secondly, it imposes a stress on the patient. The cable connection also poses a risk of improper connection. In addition, the system is subjected to electrical stray fields; this is critical because of the extremely low signal potentials that must be detected. In addition, gluing the electrodes to the sensitive skin of newborns or infants and their subsequent removal is also a problem.

The combination of several electrodes into a single relatively rigid arrangement that can be mounted as a whole on the head of a person is known from U.S. Pat. No. 4,706,679 for the purpose of electroencephalography. In that patent, a frame is provided with a plurality of spring-loaded legs that have electrodes at their ends, and serves to pick up electrical brain potentials. In the known system, the frame is designed especially for mounting on the back of a patient chair in which the patient lies for the electroencephalogram. However, this prior art provides no suggestion for performing brainstem audiometry using electrodes combined in such fashion with an acoustic stimulator and a signal generator that produces the stimulating signal, or for deriving and evaluating the evoked brainstem signs.

From U.S. Pat. No. 5,954,667 a system is known, which allows a faster and simpler detection as a result of reuse of the electrodes forming part of the system and as a result of the fact that the electrodes are maintained in mutually fixed positions. Due to the extending arms the electrodes may however still present some difficulties during operation. The electrodes may moreover be difficult to clean, as they are located on a number of arms extending from a frame.

It is therefore an object of the invention to provide a device that permit simpler and easier mounting on the head of the individual subject.

SUMMARY OF THE INVENTION

In the device according to the invention, the electrodes are combined into an arrangement with an ear cushion that allows for a much easier mounting of the device on the individual's head. Furthermore, the integration of the electrode in the cushion provides for cleaning in a simpler manner.

In a preferred embodiment the cushion forms an ear bud on a headphone comprising a output transducer for delivering and output signal to the ear.

In one embodiment the structure comprises a headband, which at an area at its end opposite the structure is adapted for abutting the subject's head opposite the ear presently being tested, hereby supporting the structure in a stable position. This provides for safe positioning of the single ear measuring device.

Preferably the structure comprises two interconnected parts each comprising a cushion and where the two interconnected parts are connected by means of a headband. This provides for a measuring on both ears without having to remove or replace the structure. The invention is especially convenient in this situation as very few elements extend from the structure, which could provide problems during mounting.

Preferably a further electrode is mounted in connection with the headband. This electrode is adapted for measuring the brainstem potentials at the crown of the head.

In a preferred embodiment each cushion is releasably connected to the remaining structure by means of a conductive coupling. This could be a snap button connection, a magnetic connection or a Velcro-type connection.

Preferably the electrode unit also contains as integrated components the acoustic converter that serves as the stimulator in the form of a loudspeaker or a bone-conduction sound source.

In the device according to the invention, the electrode unit can also include an electroencephalograph ("EEG") amplifier as a component, so that a minimum conduction path is provided between the pickup electrodes and the ERG amplifier, and thus the possibility of stray potentials being picked up is minimized.

DETAILED DESCRIPTION OF THE INVENTION

The device according to FIGS. 1–5 consists of a headband 1 with an earphone 8 at each end of the headband, and an EEG amplifier (not shown).

Figure 1:
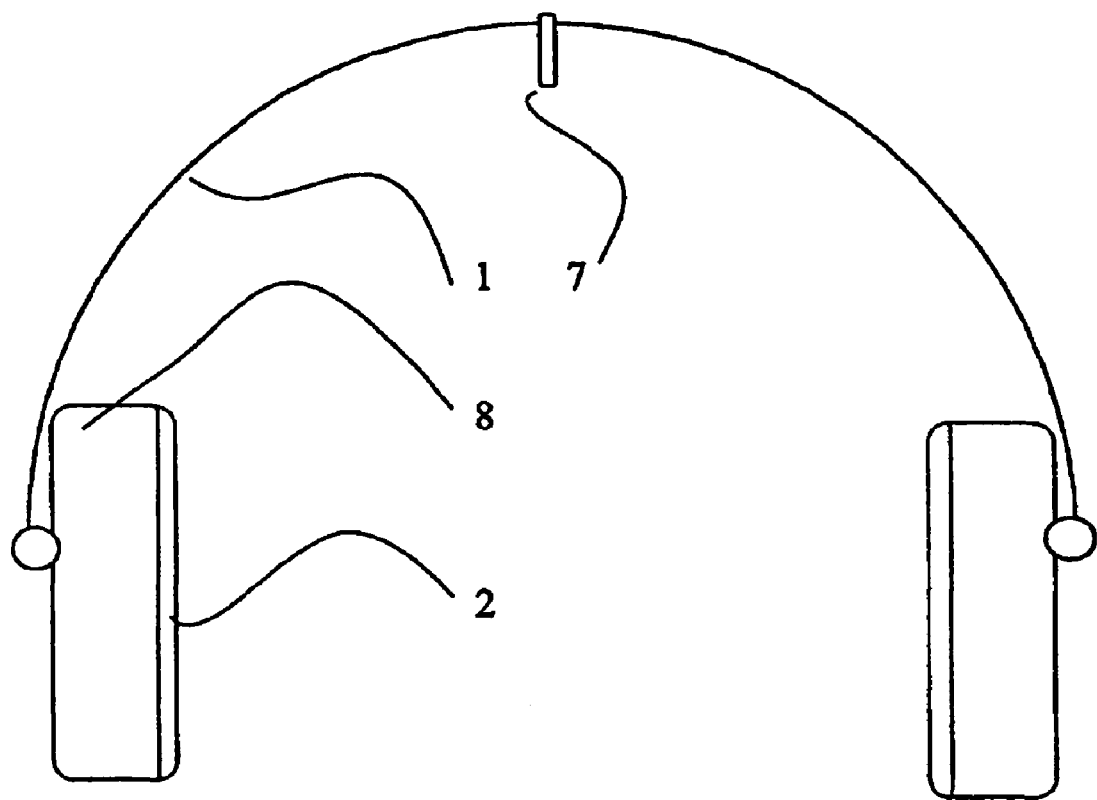
FIG. 1 is a front view of a device according to the invention.
Figure 2:
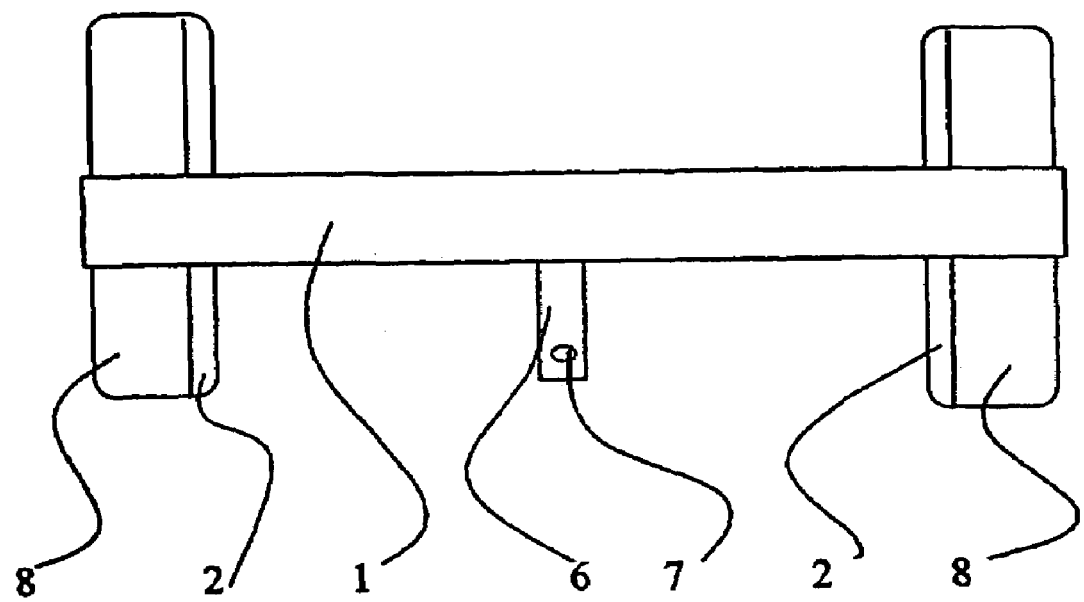
FIG. 2 is a top view of a device according to the invention.
Figure 3:
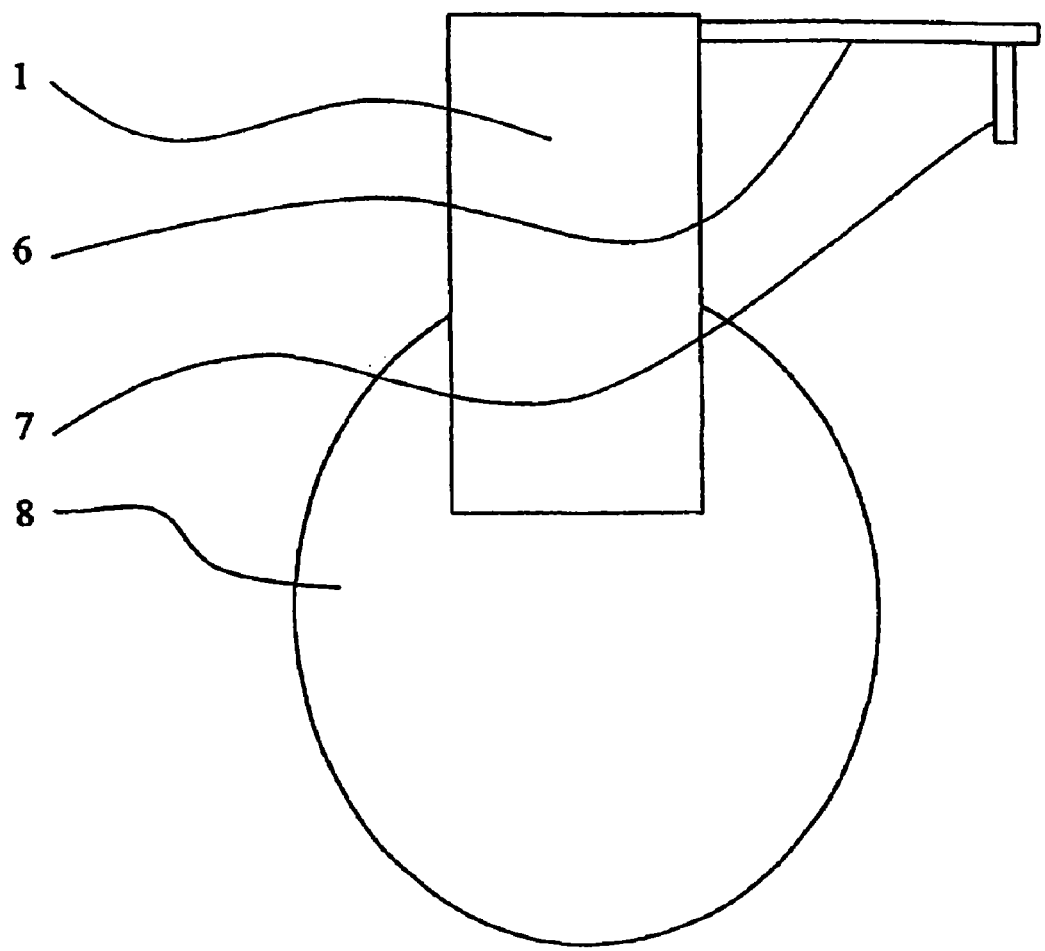
FIG. 3 is a side view of a device according to the invention.
Figure 4:
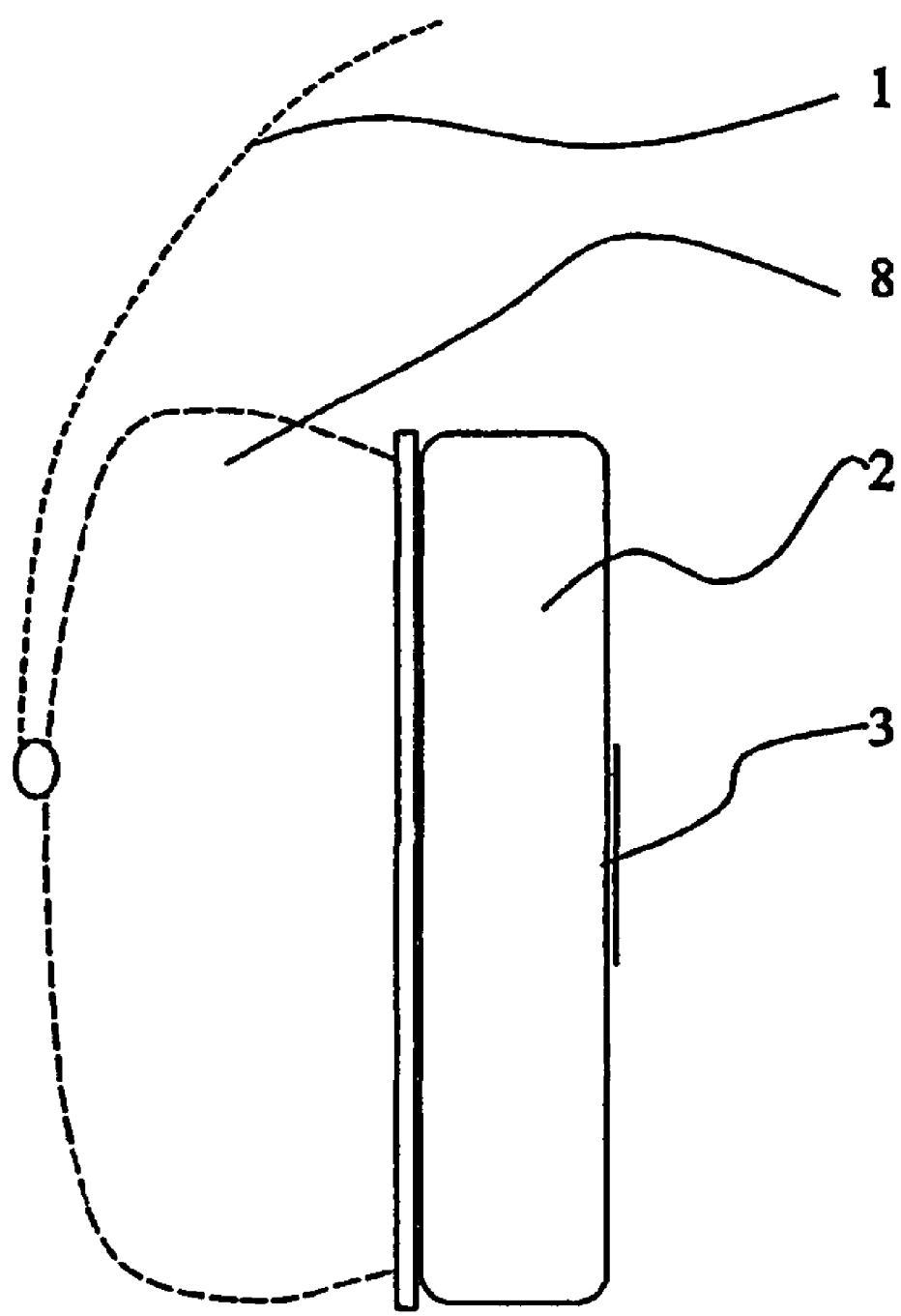
FIG. 4 is an enlarged front view of a part of the device.
Figure 5:
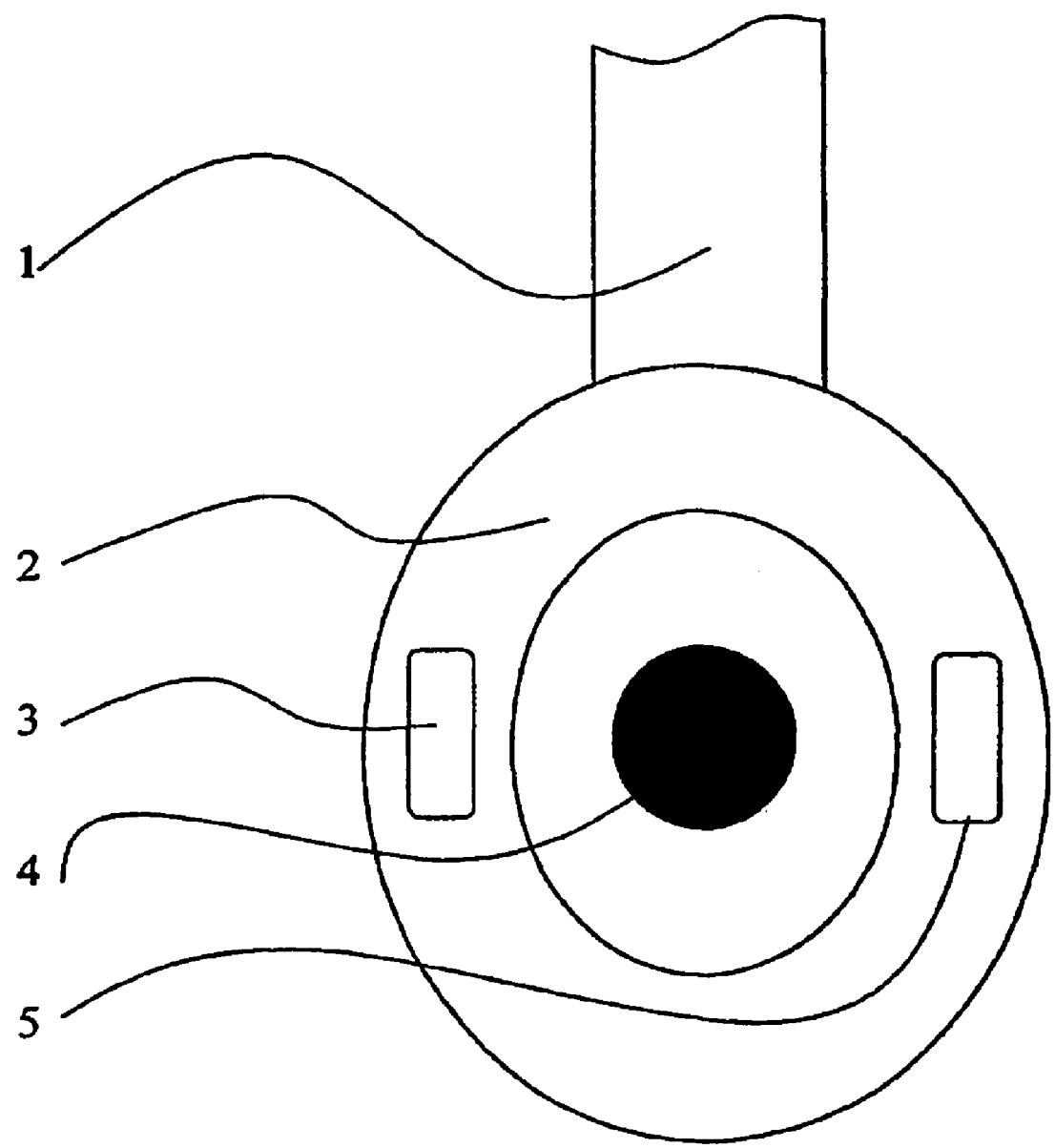
FIG. 5 is side view of apart of the device.

The views of FIGS. 1, 2 and 3 show the headphone from the front, from above, and from the side. The pickup electrode 7 is depicted in the drawings. The electrode is provided on a protruding part 6 on the headband. From FIG. 5 the earphone is shown from a different angle, namely the side facing the head during measurement. The electrodes 3 and 5 appear from this drawing. It appears that the electrodes are flat and integrated in (mounted on) an ear cushion 2 on each earphone 8.

A cable (not shown) connects the device with the rest of the audiometer used for brainstem audiometry, said audiometer generating the signals for acoustic stimulation of the ear and processing and evaluating the derived brainstem potentials. In the embodiment, a single cable that can contain both a line to supply electrical stimulation signals and also a line to conduct the preamplified brainstem potentials from EEG amplifier. Of course, separate cables or wireless transmission pathways can also be used for the purpose.

In the earphone, an electroacoustic sound converter, in other words a loudspeaker 4, is incorporated. Instead of earphone with loudspeaker, or in addition thereto, the device can be equipped with a bone conduction earpiece so that acoustic stimulation of the ear can take place either by conduction through air or conduction though bone.

The electrical potentials generated in the brainstem by acoustic stimulation of the ear are picked up by electrodes mounted on the ear cushions of the headset as well as on the headband of the headset. Usually three electrodes are used for each ear, namely a reference electrode for detecting a reference potential and two pickup electrodes. The reference electrode is brought into contact with the head in front of the ear, and one of the two deriving electrodes is placed behind the ear and the other in the sea of the crown of the head. The pickup electrode at the crown of the head is used for both sides measurement.

In the embodiment according to FIG. 1, electrode 7 is the pickup electrode that detects brainstem potentials in the vicinity of the crown of the head and electrode 3 is the reference electrode. The second pickup electrode 5 is applied to the head behind the ear. The latter electrodes appear from FIG. 5.

By integrating the electrodes into the ear cushions the mounting of the device is significantly facilitated. The cleaning of the device is furthermore greatly facilitated. In the event of a need to replace the ear cushion or the electrode due to wear, the cushions are preferably mounted releasably by means of a conductive coupling capable of transmitting the signals obtained.

The earphone with an ear cushion has the advantage that stimulation of the ear by means of loudspeaker takes place with exclusion of ambient noise. Using an earphone also makes it possible to mount a microphone inside the earphone as well, the microphone measuring the sound pressure in the earphone. As a result, during evaluation, the acoustic signal presented to the ear as an actual value signal can be checked and related directly to the time and quantity of the brainstem potentials picked up as a reaction. At the same time, the influence of any ambient noises penetrating the earphone can be measured. This microphone could also be used for the purpose of additional or simultaneous measurement of OAE (Otoacoustic emissions).

The earphone is of course adapted in terms of its shape and orientation to the elongated shape of the ear and its spatial orientation relative to the measuring points for the brainstem potentials. In order to make it possible to use the single ear measurement device for both the left and right ears, the earphone is preferably mounted rotatably on the headband so that its orientation relative to the frame can be adjusted as required for the right or left ear.

The device according to the invention comprises a signal generator/signal evaluation unit, an electrode unit, and a stimulator.

A cable connects the EEG amplifier and thus the electrode unit with a signal generator/evaluation unit that is also connected by a cable with a stimulator.

Signal generator/evaluation unit generates and transmits electrical stimulation signals to a stimulator, which the latter converts into a series of acoustic signals and then transmits them. The electrode unit mounted on the head of the subject picks up the potentials evoked by the brainstem, which are then amplified by the EEG amplifier and fed to signal generator/evaluation unit 1 where they are evaluated.

Another embodiment of the stimulator that is not shown separately consists in using a bone conduction earphone, as is known of itself.

Instead of only an EEG amplifier, the complete device for measuring the derived brain potentials can be mounted on the frame of electrode unit. Signal transmission between electrode unit and signal generator/evaluation unit can also be performed without wires instead of using the cable connection shown in the embodiment. In addition, the series of stimulating clicks and the acquisition of measured values can be triggered in a wireless fashion by operating a switch on the electrode unit.

The invention claimed is:

1. A device for determining acoustically evoked brain potentials in brainstem audiometry, the device comprising: a plurality of electrodes comprising at least one pickup electrode and a reference electrode, to be applied at different points on a subject's head, a structure mounting the electrodes in fixed positions in relation to each other, said structure comprising a flexible cushion for abutting the head of the subject around an ear, and wherein the pickup electrode and the reference electrode are integrated in the flexible cushion.

2. A device according to claim 1, where the cushion forms an ear bud on a headphone comprising a output transducer for delivering and output signal to the ear.

3. A device according to claim 1, where two cushions are provided, where the structure comprises two interconnected parts each comprising a cushion and where the two interconnected parts are connected by means of a headband.

4. A device according to claim 1, where the structure comprises a headband, which at an area at its end opposite the structure is adapted for abutting the subject's head opposite the ear presently being tested hereby supporting the structure in a stable position.

5. A device according to claim 4, where a further electrode is mounted in connection with the headband.

6. A device according to claim 1, wherein each cushion is releasably connected to the remaining structure by means of a conductive coupling.

7. A device for determining acoustically evoked brain potentials in brainstem audiometry, the device comprising a plurality of electrodes comprising at least one pickup electrode and a reference electrode for application against different points of a subject's head, and a structure for mounting the electrodes in fixed positions in relation to each other, the structure comprising a flexible cushion for abutting the head of the subject around an ear, the electrodes being flat and mounted on surface parts of the flexible cushion so as to abut the head of a subject.

* * * * *